(12) United States Patent
Al-Jumaia et al.

(10) Patent No.: US 12,279,896 B2
(45) Date of Patent: Apr. 22, 2025

(54) TALKING DENTAL GLOVE

(71) Applicant: Imam Abdulrahman Bin Faisal University, Dammam (SA)

(72) Inventors: Ayman Mansour Al-Jumaia, Dammam (SA); Abdul-Hakeem Alomari, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 532 days.

(21) Appl. No.: 17/869,383

(22) Filed: Jul. 20, 2022

(65) Prior Publication Data
US 2024/0023900 A1    Jan. 25, 2024

(51) Int. Cl.
*A61B 5/00* (2006.01)
*A61B 5/024* (2006.01)
*A61C 17/12* (2006.01)

(52) U.S. Cl.
CPC .......... *A61B 5/741* (2013.01); *A61B 5/02438* (2013.01); *A61B 5/6806* (2013.01); *A61B 5/742* (2013.01); *A61B 5/746* (2013.01); *A61C 17/12* (2019.05); *A61B 2562/227* (2013.01)

(58) Field of Classification Search
CPC ... A61B 5/741; A61B 5/02438; A61B 5/6806; A61B 5/742; A61B 5/746; A61B 2562/227; A61B 5/165; A61B 5/4542; A61C 17/12
See application file for complete search history.

(56) References Cited

U.S. PATENT DOCUMENTS

| | | | | |
|---|---|---|---|---|
| 10,319,257 | B2* | 6/2019 | Bavunoglu | ............ G06F 3/162 |
| 2006/0079794 | A1* | 4/2006 | Liu | ...................... A61B 5/6806 |
| | | | | 600/502 |
| 2016/0132109 | A1* | 5/2016 | Hardin | ................... G06F 3/014 |
| | | | | 345/156 |
| 2016/0284236 | A1* | 9/2016 | Bavunoglu | ............ G06F 3/014 |

FOREIGN PATENT DOCUMENTS

KR    10-2009150    8/2019

OTHER PUBLICATIONS

Fantin, et al. ; Smart Communication Haptic Glove for Deaf and Dumb People ; International Journal of Scientific Research and Review, vol. 8, Issue 3 ; 2019 ; 6 Pages.

* cited by examiner

*Primary Examiner* — Jonathan T Kuo
(74) *Attorney, Agent, or Firm* — Oblon, McClelland, Maier & Neustadt, L.L.P.

(57) ABSTRACT

The present disclosure provides a talking glove to aid communication between a medical practitioner and a patient while the patient is undergoing a dental/medical treatment. The talking glove may be a dental glove worn by the patient and/or a dental practitioner and includes a plurality of contact sensors, where each contact sensor is located on a different finger position of the talking dental glove; a suction button; a pulse rate sensor configured to generate pulse rate signals; an LCD screen; a speaker; a power source; and a microcontroller connected to the power source, the plurality of contact sensors, the pulse rate sensor, the LCD screen, and the speaker. Each of these components is disposed on an outer surface of the talking dental glove.

19 Claims, 12 Drawing Sheets

TALKING DENTAL GLOVE

BACKGROUND

Technical Field

The present disclosure is directed to a glove that may be worn on one hand and used to communicate messages during use, in particular a glove for use by a patient or medical practitioner during medical and/or dental treatment.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

A typical problem with human teeth is tooth decay. It is well known that a common method of treating tooth decay involves anesthetizing a local area, using a mechanical drill (or similar equipment) to remove a decayed portion of the tooth to form a cavity area, placing a restorative material in the cavity area, and curing the restorative material. This treatment method requires a patient to hold the mouth wide open during the treatment, while a dentist inserts various tools into the mouth to treat the tooth decay. In such condition, the patient may not be able to communicate with the dentist regarding a degree of discomfort or pain during the treatment.

Accordingly, it is one object of the present disclosure to provide a talking dental glove, and methods for using a talking dental glove to communicate with the dentist during the dental treatment.

SUMMARY

In an exemplary embodiment, a talking dental glove is provided. The talking dental glove includes a plurality of contact sensors, where each contact sensor is located on a different finger position of the talking dental glove; a suction button; a pulse rate sensor configured to generate pulse rate signals; an LCD screen; a speaker; a power source; and a microcontroller connected to the power source, the plurality of contact sensors, the pulse rate sensor, the LCD screen, and the speaker. Each of these components is disposed on an outer surface of the talking dental glove.

In another exemplary embodiment, a method for using a talking dental glove for communication between a dentist and a patient wearing the talking dental glove is provided. The method includes generating a contact signal by touching a trigger contact sensor to any one of a plurality of fingertip contact sensors and a plurality of center finger contact sensors; receiving the contact signal, by a microcontroller located on a wristband of the talking dental glove and electrically connected to a power source and to each of the trigger contact sensor, the plurality of fingertip contact sensors, and the plurality of center finger contact sensors; determining, by the microcontroller, a contact pattern from the contact signal; searching, by the microcontroller, a database stored in a memory of the microcontroller, where the database includes records linking contact patterns of a plurality of contact sensors to messages; matching, by the microcontroller, the contact pattern to a message in the database; and generating, by the microcontroller, drive signals to actuate a speaker located on the talking dental glove to reproduce the message.

In another exemplary embodiment, a method for assembling a talking dental glove is provided. The method includes receiving the talking dental glove having a glove body, a thumb finger sheath, an index finger sheath, a middle finger sheath, a ring finger sheath, and a pinky finger sheath, and a wristband; attaching a microcontroller to the wristband; attaching a power supply to the wristband; electrically connecting the power supply to the microcontroller; attaching an LCD screen to the wristband; electrically connecting the LCD screen to the power supply; connecting the LCD screen to the microcontroller; attaching a speaker to the wristband; electrically connecting the speaker to the power supply; connecting the speaker to the microcontroller; attaching a trigger contact sensor to a thumb pad position of the thumb finger sheath; electrically connecting the trigger contact sensor to the microcontroller; attaching each of a plurality of fingertip contact sensors to a fingertip position of a different one of the index finger sheath, the middle finger sheath, the ring finger sheath, and the pinky finger sheath; electrically connecting each of the plurality of fingertip contact sensors to the microcontroller; attaching each of a plurality of center finger contact sensors to a region between the glove body and the fingertip position of the index finger sheath, the middle finger sheath, the ring finger sheath, and the pinky finger sheath; electrically connecting each of the plurality of fingertip contact sensors to the microcontroller; attaching a suction button to a side position of the glove body beneath a base of the index finger sheath; electrically connecting the suction button to the microcontroller; and attaching the microcontroller to a valve of a mouth fluid suction tool, where the valve is configured to control a vacuum of the mouth fluid suction tool, and where the microcontroller is configured to actuate the valve to control the vacuum when the trigger contact sensor touches the suction button.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
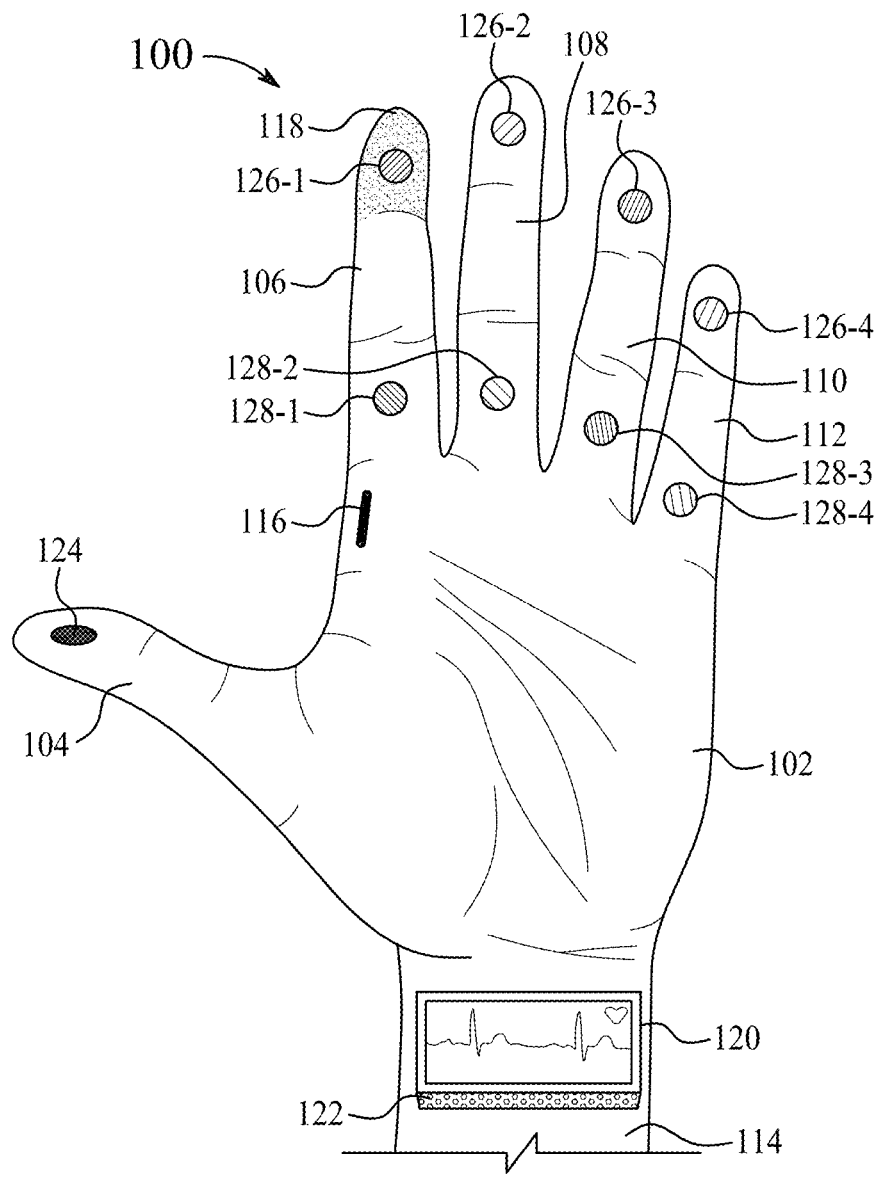
FIG. 1 is an exemplary talking dental glove, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a talking dental glove and a method of using the talking dental glove for communication between a dentist and a patient wearing the talking dental glove. The talking dental glove generates speech signals based on a pattern of finger to thumb contact. The talking dental glove includes a plurality of contact sensors, a heart rate monitor, a display screen which displays a heart rate, a speaker and a valve connected to a mouth fluid suction tool to allow the patient to control an amount of suction. A microcontroller is connected to the contact sensors, a switch of the mouth fluid suction tool, a power source, the display, and the heart rate monitor. FIG. 1 illustrates an exemplary talking dental glove 100 (hereinafter referred to as "the glove 100"), according to an aspect of the present disclosure. The glove 100 includes a glove body 102, a thumb finger sheath 104, an index finger sheath 106, a middle finger sheath 108, a ring finger sheath 110, and a pinky finger sheath 112 each connected to the glove body 102. In a non-limiting example, the glove body 102 and each of the finger sheaths extending from the glove body 102 may be made of one fabric, selected from the group of latex, nitrile, polyurethane, polyester, nylon, leather, PVC, or a combination thereof. The glove 100 also includes a wristband 114 connected to the glove body 102, a plurality of contact sensors attached to the thumb and finger sheaths, a suction button 116, a pulse rate sensor 118 (indicated by the grey dotted area at the end of the index finger 106) configured to generate pulse rate signals, a liquid crystal display (LCD) screen 120, and a speaker 122. Each contact sensor is located on a different finger position of the glove 100. In an aspect, the plurality of contact sensors includes a pulse rate sensor 118 located on the index finger sheath 106 at a fingertip position, a trigger contact sensor 124 located on a thumb sensor position of the thumb finger sheath 104, a plurality of fingertip contact sensors 126, and a plurality of center finger contact sensors 128.

The contact sensor located on the thumb finger may be referred to as the primary sensor, whereas the contact sensors located on the remaining fingers may be referred to as the secondary sensors.

Each of the fingertip contact sensors 126 is connected to a fingertip position of each of the index finger sheath 106, the middle finger sheath 108, the ring finger sheath 110, and the pinky finger sheath 112. For example, an index finger fingertip contact sensor 126-1 is connected to the index finger sheath 106, a first fingertip contact sensor 126-2 is connected to the fingertip position of the middle finger sheath 108, a second fingertip contact sensor 126-3 is connected to the fingertip position of the ring finger sheath 110, and a third fingertip contact sensor 126-4 is connected to the fingertip position of the pinky finger sheath 112. Each of the center finger contact sensors 128 is connected to a region between the glove body 102 and the fingertip position of each of the index finger sheath 106, the middle finger sheath 108, the ring finger sheath 110, and the pinky finger sheath 112. For example, a first center finger contact sensor 128-1 is connected to a region between the glove body 102 and the fingertip position of the index finger sheath 106, a second center finger contact sensor 128-2 is connected to a region between the glove body 102 and the fingertip position of the middle finger sheath 108, a third center finger contact sensor 128-3 is connected to a region between the glove body 102 and the fingertip position of the ring finger sheath 110, and a fourth center finger contact sensor 128-4 is connected to a region between the glove body 102 and the fingertip position of the pinky finger sheath 112.

In an aspect, the suction button 116 is located on a side of the glove body 102 and beneath a base of the index finger sheath 106. Particularly, the suction button 116 is located proximal to the base of the index finger sheath 106 such that the suction button 116 is accessible by a tip of the thumb finger sheath 104. In some aspects, the trigger contact sensor 124 may be positioned away from the tip of the thumb finger sheath 104 so as to not interfere when the tip contacts the suction button 116.

The contact sensors may be medical electrodes selected from the group comprising silver, gold, copper, stainless steel, and conductive polymer. Each medical electrode includes a lead which is wired to a battery. For example, a primary contact sensor on a thumb finger may be wired to a positive terminal of a battery and a secondary contact sensor on one of the other fingers may be wired to a negative terminal of the battery or to a ground of a microcontroller. A microcontroller may measure a current which flows along a current path of the wiring. For example, the microcontroller may be connected to the leads of each contact sensor on each secondary finger and may receive at a pin a current when the thumb finger touches the secondary contact sensor. The current path may be continued through the microcontroller to the ground.

The diameters of the contact sensors are selected from the range of 0.25 cm, 0.5 cm, 1.0 cm, 1.5 cm and 2 cm. The selection of the diameter of the contact sensor is dependent on the size of the dental glove. For example, a dental glove designed for a child may have contact sensor diameters which are smaller, such as 0.25 cm or 0.5 cm, while a dental glove designed for a large hand may have contact sensor diameters in the range of 1.0 cm, 1.5 cm and 2 cm.

The contact sensors may be of a magnetic material, such as a barium ferrite magnet which includes short carbon fibers to increase the conductivity. Magnetic contact sensors may make it easier for the user to secure the contact between the thumb finger contact sensor and one of the finger contact sensors.

Figure 2A:
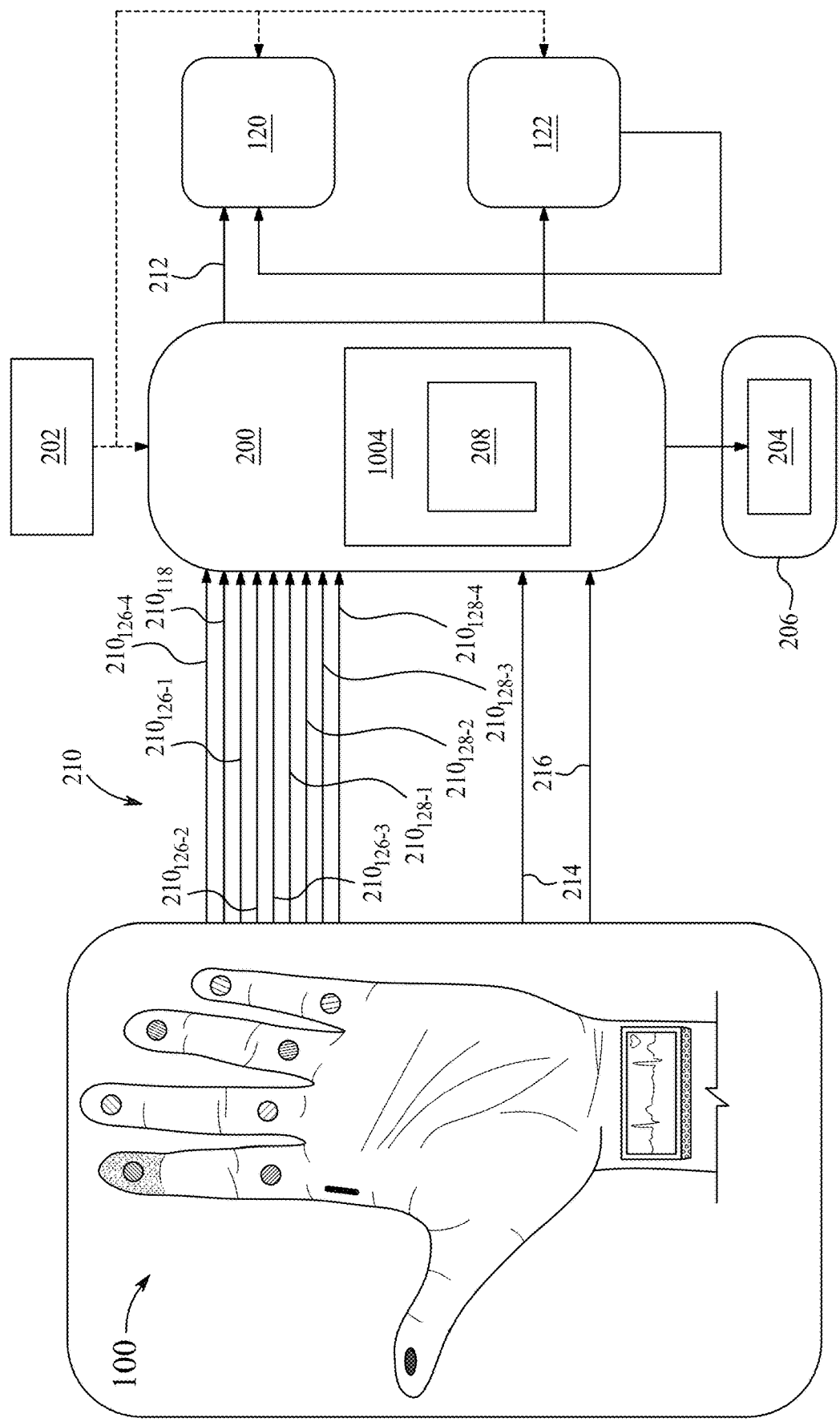
FIG. 2A is an exemplary block diagram illustrating connections between various components of the talking dental glove, according to certain embodiments.

FIG. 2A is an exemplary block diagram illustrating connection between various components of the glove 100. The glove 100 also includes a microcontroller 200 and a power source 202. The microcontroller 200 is connected to each of the power source 202, the plurality of contact sensors, the pulse rate sensor 118, the LCD screen 120, the speaker 122, and a valve 204 of a mouth fluid suction tool 206. In an aspect, the suction button 116 is connected to the valve 204 of the mouth fluid suction tool 206, where movement of the suction button 116 to the second position "P2" opens the valve 204 and creates the suction pressure at the dental aspirator. In some aspects, the mouth fluid suction tool 206 may include the dental aspirator.

The LCD screen 120 and the speaker 122 are located on the wristband 114. In some aspects, the glove 100 may include an LED display with a touchscreen. The power source 202 is configured to power the microcontroller 200, each of the plurality of contact sensors, the pulse rate sensor 118, the LCD screen 120, the speaker 122, and the valve 204. In one aspect, the power source 202 may be a button cell battery. In another aspect, the power source 202 may be a power cord connected to an electrical outlet. In some aspects, the valve 204 may be an electrically actuated valve. Although the components are illustrated through individual blocks, the microcontroller 200, the LCD screen 120, the speaker 122, and the power source 202 are an integral part of the glove 100. In an aspect, the power source 202 may be embedded in the glove body 102. A space for inserting the power source 202, such as the button cell battery or the power cord, may be accessible on an outer surface of the glove 100.

The microcontroller 200 includes a memory 1004 (see FIG. 10) and a database 208 stored in the memory 1004. The database 208 includes records linking contact patterns of the plurality of contact sensors to messages related to a contact pattern. The glove 100 of FIG. 1A is configured to generate the contact pattern when the trigger contact sensor 124 contacts one of the plurality of contact sensors. In an aspect, the contact of the trigger contact sensor 124 and one of the plurality of contact sensors may generate a haptic feedback to the patient, so that the patient is aware that the contact is successful. Referring back to FIG. 2, in an aspect, the microcontroller 200 is configured to receive each contact pattern (collectively indicated by the reference numeral 210 and individually referenced as $210_{118}$, $210_{126-1}$, $210_{126-2}$, $210_{126-3}$, $210_{126-4}$, $210_{128-1}$, $210_{128-2}$, $210_{128-3}$, $210_{128-4}$, perform a search in the database 208, and match the contact pattern to one message in the database 208. The microcontroller 200 is further configured to generate drive signals (indicated by the reference numeral 212) to actuate the speaker 122 to reproduce the message.

In an aspect, the microcontroller 200 is further configured to receive the pulse rate signals (indicated by the reference numeral 214) from the pulse rate sensor 118, determine a heart rate from the pulse rate signals 214, render the heart rate and the pulse rate signals 214 on the LCD screen 120, and determine whether the heart rate exceeds a heart rate threshold. When the heart rate exceeds the heart rate threshold, the microcontroller 200 may be configured to actuate the speaker 122 to generate an audible alert and render a visual alert (as shown in FIG. 2) on the LCD screen 120. In some aspects, an age of the patient and other health history may be provided as inputs to the microcontroller 200 via an input unit (not shown). When the display is embodied as an LED display with touchscreen, the LED display may provide options regarding the health history to choose. Based on the age and health history, the heart rate threshold may be determined. In some aspects, various heart rate thresholds for a combination of ages and a health history may be stored in the database 208 and the microcontroller 200 may be configured to obtain the heart rate threshold from the database and compare it with the instantaneous heat rate measured by the pulse rate sensor 118 during a dental treatment. When a value of the heart rate is greater than the obtained heart rate threshold (that is, abnormal heart rate) the microcontroller 200 may provide the visual alert and audio alert as described above. The pulse rate sensor 118 in the glove 100 is beneficial during the dental treatment/dental surgery since there may be a possibility of heart palpitations due to: (a) stress that leads to high blood pressure and causes changes to the heart, such as palpitations and (b) anxiety that leads to high levels of adrenaline, which causes atrial fibrillation in patients. It is known that the presence of adrenaline (also known as epinephrine) narrows the blood vessels, which can cause heart palpitations.

In another aspect, the suction button 116 may be embodied as touch button and may be connected to the microcontroller 200. The valve 204 is configured to control a vacuum of the mouth fluid suction tool 206. The microcontroller 200 is connected to the valve 204 and is configured to actuate the valve 204 to control the vacuum when the trigger contact sensor 124 touches the suction button 116. An input signal 216 may be generated to the microcontroller 200 based on the contact between the trigger contact sensor 124 and the suction button 116.

Figure 2B:
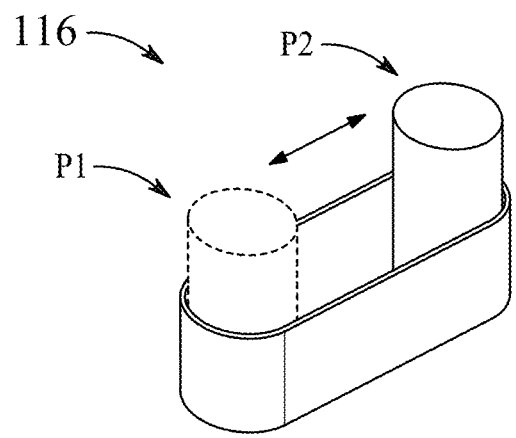
FIG. 2B is an exemplary suction button of the talking dental glove, according to certain embodiments.

FIG. 2B illustrates an exemplary view of the suction button 116. In an aspect, the suction button 116 may be embodied as a slide button configured to slide between a first position "P1" and a second position "P2". The suction button 116 may be configured to automatically return to the first position "P1" when released thumb releases the suction button 116 at the second position "P2". In an aspect, the suction button 116 may be operably connected to a dental aspirator (not shown). A duration of a suction created at the dental aspirator may be equal to a duration for which the suction button 116 is retained at the second position "P2". Once the suction button 116 moves out of the second position "P2", the suction at the dental aspirator may be stopped. As such, a patient wearing the glove 100 may control the operation of the dental aspirator. As used herein, the term "operably connected" may include various connections, for example hydraulic connection or pneumatic connection, including wires or tubes, present between the suction button 116 and the dental aspirator which aids actuation of the dental aspirator based on position of the suction button 116.

Figure 2C:
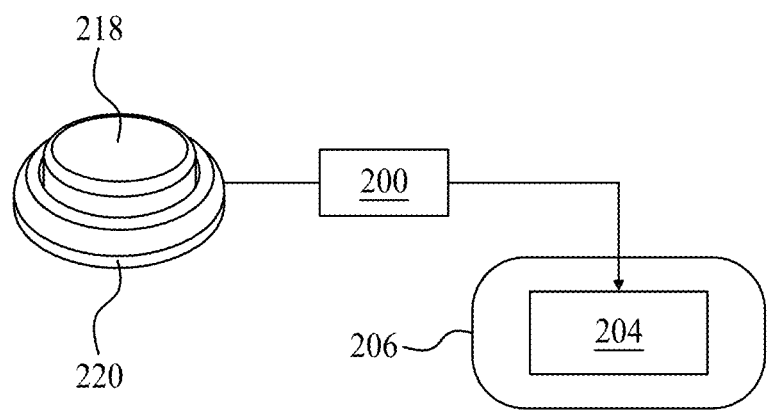
FIG. 2C is an exemplary illustration of a suction button, according to certain embodiments.

FIG. 2C is an exemplary illustration of the suction button 116, according to another aspect of the present disclosure. The suction button 116 may be embodied as a push button and may be connected to the valve 204 of the mouth fluid suction tool 206 via the microcontroller 200 as shown in FIG. 2C. The push button may be configured to be actuated from a rest condition (corresponding to a state illustrated in FIG. 2C) to a pushed or pressed condition. As used herein, the phrase "pushed condition or pressed condition" refers to a condition where a button portion 218 is pressed into a button housing 220. A duration of a suction created in the mouth fluid suction tool 206 (such as the dental aspirator) may be equal to a duration for which the button portion 218 is retained in the pressed condition. Once the button portion 218 returns to the rest condition, the suction at the dental aspirator may be stopped. In some aspects, the button portion 218 may be connected to, via the microcontroller 200, a switch that is configured to operate the valve 204 of the mouth fluid suction tool 206.

Figure 3:
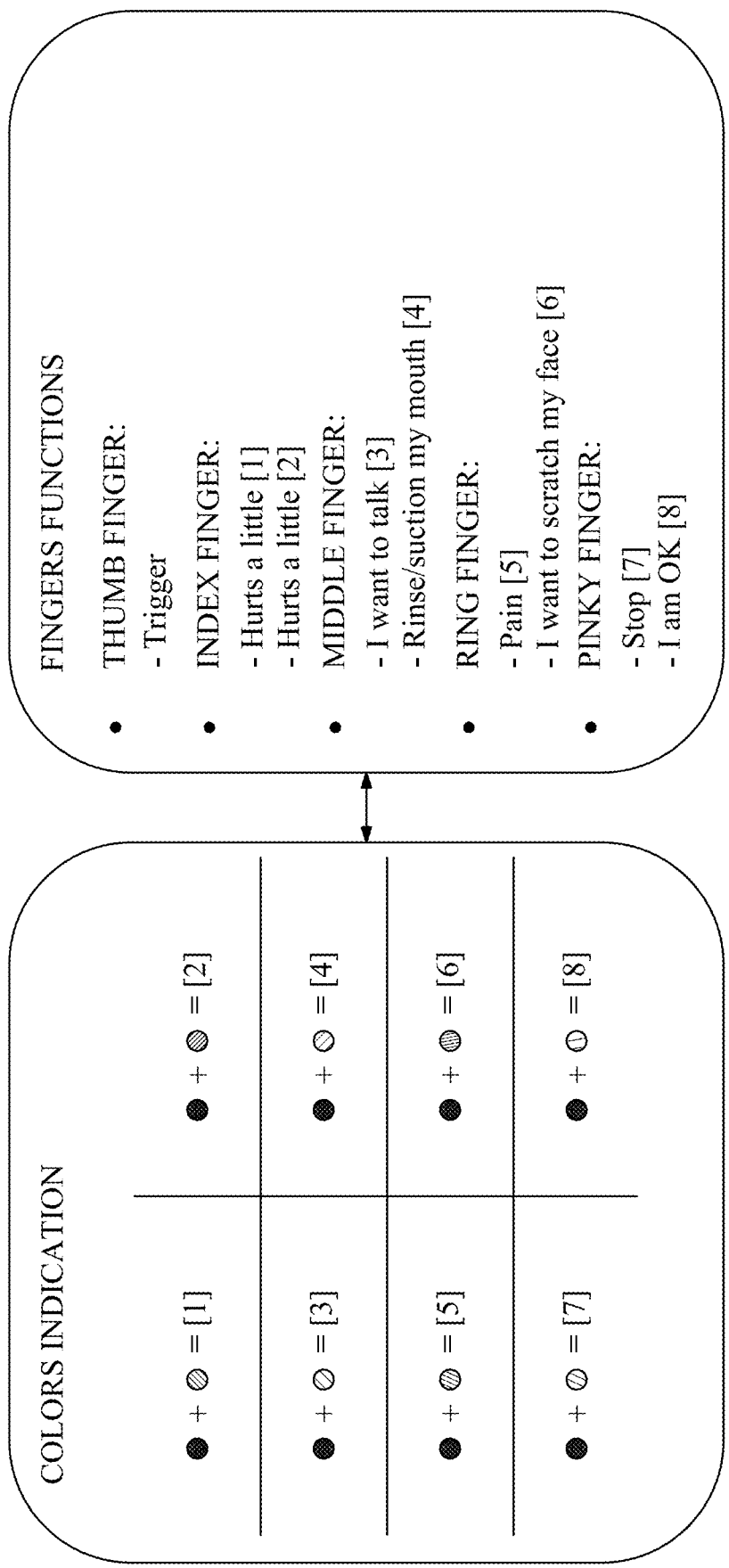
FIG. 3 is an exemplary illustration of contact patterns and corresponding messages that may be generated using the talking dental glove, according to certain embodiments.

FIG. 3 illustrates exemplary contact patterns and associated messages, according to aspects of the present disclosure. In an aspect, the contact pattern includes signals generated by touching the trigger contact sensor 124 to one of the fingertip contact sensors 126 on the index finger sheath 106, the middle finger sheath 108, the ring finger sheath 110, and the pinky finger sheath 112. The contact pattern further includes signals generated by touching the trigger contact sensor 124 to one of the center finger contact sensors 128 on the index finger sheath 106, the middle finger sheath 108, the ring finger sheath 110, and the pinky finger sheath 112. Each of such contacts generates a corresponding message and as described earlier, the microcontroller 200 is configured to render the message on the speaker 122. In some aspects, the microcontroller 200 may be configured to render the message on the LCD screen 120.

In an aspect, the microcontroller 200 may be configured to generate the drive signals to actuate the speaker 122 to reproduce:
  (i) a first message when the trigger contact sensor 124 touches an index finger fingertip contact sensor 126-1;
  (ii) a second message when the trigger contact sensor 124 touches a middle finger fingertip contact sensor, such as the first fingertip contact sensor 126-2;
  (iii) a third message when the trigger contact sensor 124 touches a ring finger fingertip contact sensor, such as the second fingertip contact sensor 126-3;
  (iv) a fourth message when the trigger contact sensor 124 touches a pinky finger fingertip contact sensor, such as the third fingertip contact sensor 126-4;
  (v) a fifth message when the trigger contact sensor 124 touches an index finger center finger contact sensor, such as the first center finger contact sensor 128-1;
  (vi) a sixth message when the trigger contact sensor 124 touches a middle finger center finger contact sensor, such as the second center finger contact sensor 128-2;
  (vii) a seventh message when the trigger contact sensor 124 touches a ring finger center finger contact sensor, such as the third center finger contact sensor 128-3; and
  (viii) an eighth message when the trigger contact sensor 124 touches a pinky finger center finger contact sensor, such as the fourth center finger contact sensor 128-4.

Upon contact by the trigger contact sensor 124, the index finger fingertip contact sensor 126-1 may be configured to produce the first message which may be heard as "Hurts a little". Similarly, the second message may be "Hurts a lot"; the third message may be "I want to talk"; the fourth message may be "Rinse/suction my mouth"; the fifth message may be "pain"; the sixth message may be "I want to scratch my face"; the seventh message may be "Stop"; and the eight message may be "I am ok". When the patient is being treated for dental issues, the dentist operates on the teeth where the mouth of the patient needs to be kept wide open. As such, the patient may not be able to convey any message to the dentist orally. In such instances, the glove 100 of the present disclosure aids communication between the patient and the dentist. The messages described above are useful for the patient to immediately convey important messages to the dentist during the dental treatment. The messages described above exemplary and should not be construed as limiting. In an aspect, each of these messages may be reproduced by the speaker 122 once based on a single instance contact of the trigger contact sensor 124 with the corresponding contact sensor. The single instance contact may be for a prolonged duration. In another aspect, the same message may be repeated continuously during the prolonged duration of contact of the trigger contact sensor 124 with the corresponding contact sensor. In some aspect, the message can be truncated as soon as the contact between the trigger contact sensor 124 and the corresponding contact sensor is stopped. In some aspects, the message may be completely reproduced irrespective of the contact between the trigger contact sensor 124 and the corresponding contact sensor being stopped at any portion of length of the message.

Figure 4:
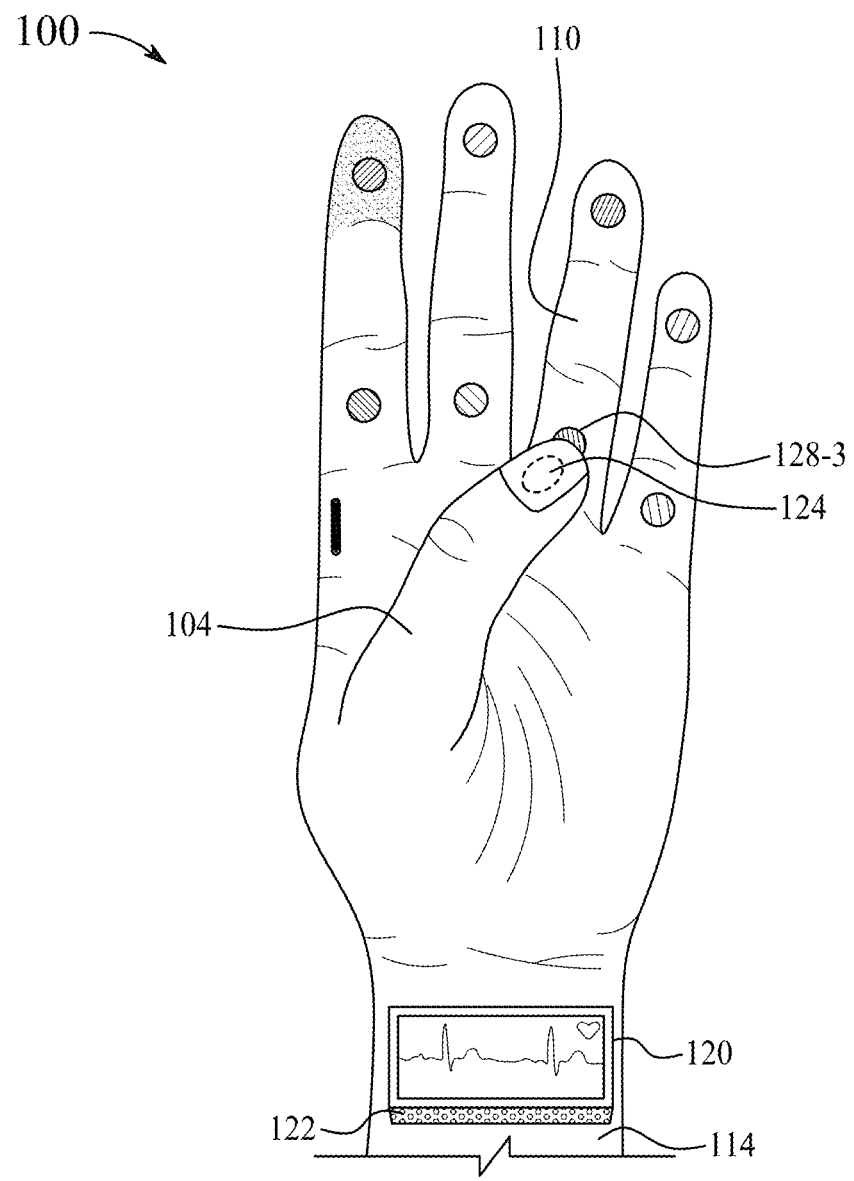
FIG. 4 illustrates a contact between two contact sensors of the talking dental glove, according to certain embodiments.

FIG. 4 illustrates an example of the contact between the trigger contact sensor 124 (shown as a dotted line, as the contact sensor is located on a pad of the thumb finger as shown in FIG. 1) and the ring finger center finger contact sensor, such as the third center finger contact sensor 128-3. Such contact generates a corresponding contact pattern which is received by the microcontroller 200. As described above, the microcontroller 200 searches the database 208 for the contact pattern and the associated message and generates the drive signal to the speaker 122 to reproduce the associated message. For the contact between the trigger contact sensor 124 and the ring finger center finger contact sensor, such as the third center finger contact sensor 128-3, the speaker 122 reproduces the seventh message from the database 208, where the patient wishes to request the dentist for a momentary "Stop". Similarly, as the patient contacts each contact sensor with the trigger contact sensor 124, a corresponding message is reproduced by the speaker 122. A chart, with details of the contact pattern and corresponding messages illustrated in FIG. 3, may be printed, and displayed in front of the patient during the dental treatment. Accordingly, the patient may make required contacts to convey desired message. Although the speaker 122 is illustrated to be located at the base of the glove body 102 corresponding to palm surface of the patient, in some aspects, the speaker 122 may be located on an opposite side. However, the patient may be suggested to place the palm in a comfortable position, such that the message reproduced by the speaker 122 is audible to the dentist.

Figure 5:
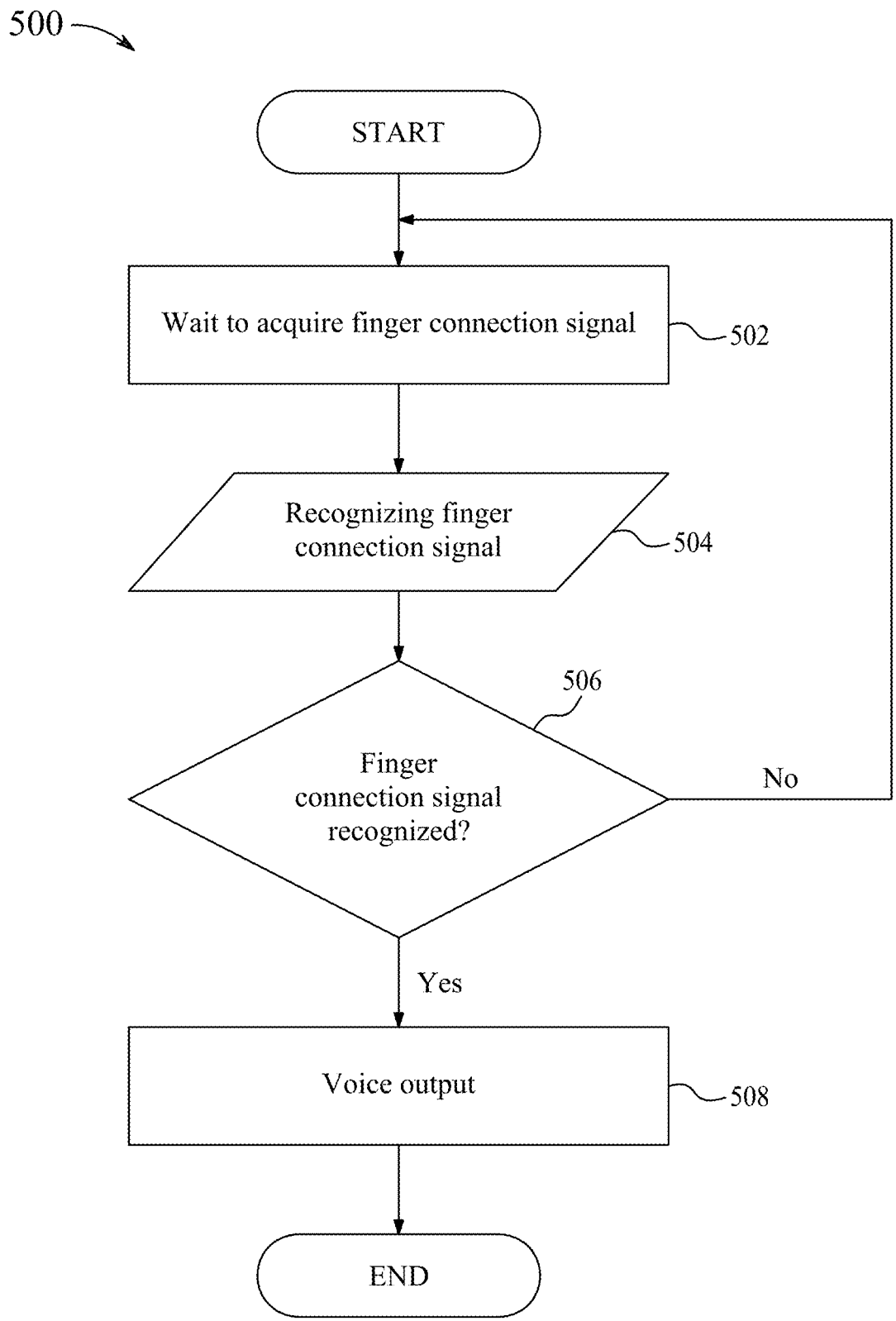
FIG. 5 is an exemplary flowchart of a method of generating voice output by the talking dental glove, according to certain embodiments.

FIG. 5 illustrates a flowchart of a method 500 implemented by the microcontroller 200, according to an aspect of the present disclosure. The method 500 is described in conjunction with FIG. 1A through FIG. 4. At step 502, the microcontroller 200 may be supplied with power by the power source 202 and waits to acquire a finger connection signal that is generated based on a connection between the trigger contact sensor 124 and each of the plurality of contact sensors.

At step 504, the microcontroller 200 is configured to recognize the finger connection signal, indicating the contact pattern.

At step 506, when the recognition of the finger connection signal is successful, the microcontroller 200 is configured to obtain a corresponding message from the database 208. If the finger connection signal is not recognized or is unsuccessful, the microcontroller 200 waits to acquire signals based on connection between the trigger contact sensor 124 and the plurality of contact sensors.

At step 508, the microcontroller 200 is configured to generate drive signals to provide a voice output which reproduces the message obtained from the database 208.

Figure 6:
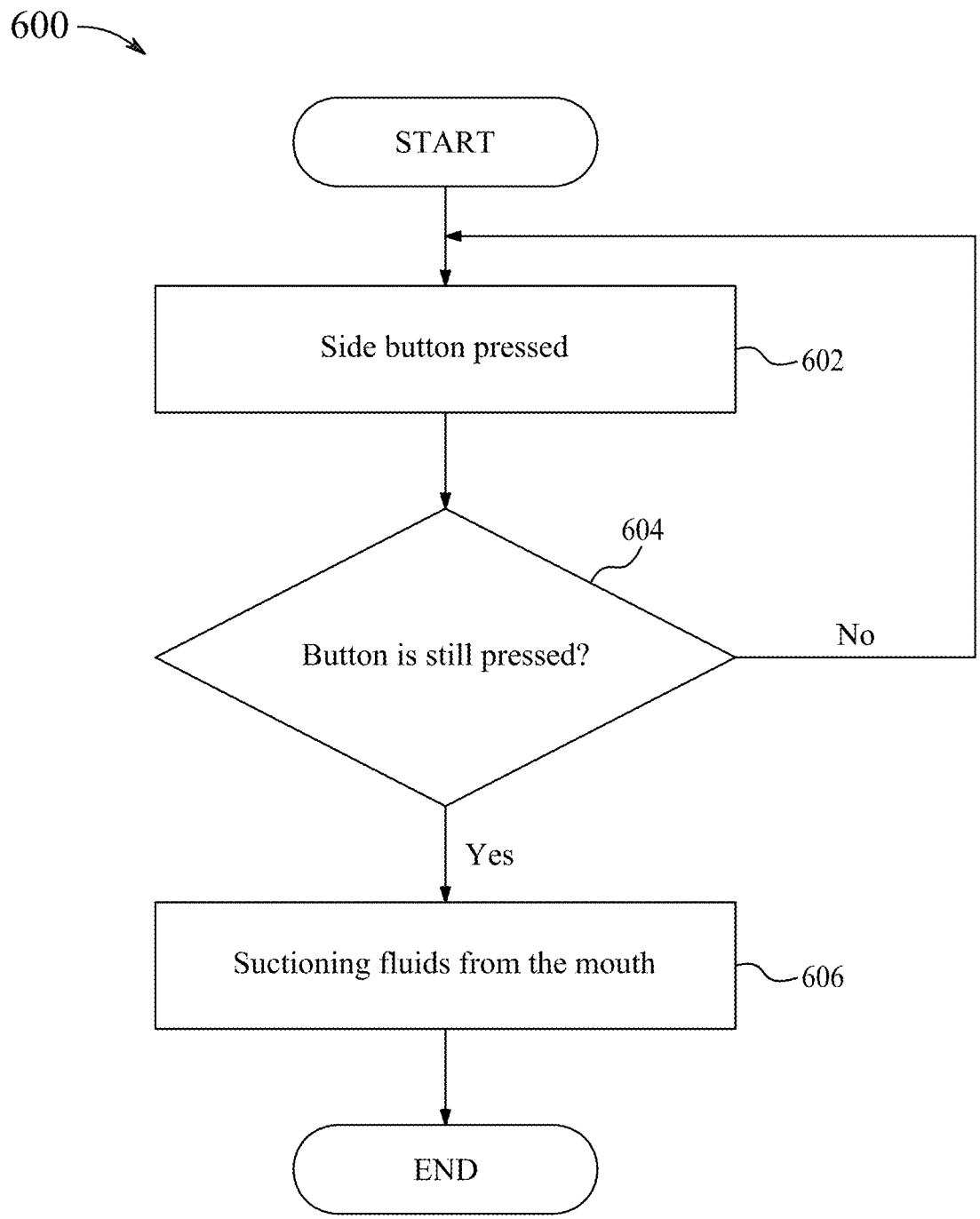
FIG. 6 is an exemplary illustration of a method of suctioning fluids from the mouth of a patient using the talking dental glove, according to certain embodiments.

FIG. 6 illustrates a flowchart of a method 600 implemented by the microcontroller 200, according to an aspect of the present disclosure. The method 600 is described in conjunction with FIG. 1A through FIG. 4. At step 602, the microcontroller 200 is configured to receive the input signal 216 when the side button, such as the suction button 116, is pressed.

At step 604, the microcontroller 200 is configured to determine if the side button is still pressed.

At step 606, the microcontroller 200 is configured to actuate the valve 204 of the mouth fluid suction tool 206 to suction fluids from the mouth of the patient, when the side button is still pressed. If the microcontroller 200 determines that the side button is not pressed for a minimum required duration, the microcontroller 200 waits to receive the input signal 216.

Figure 7:
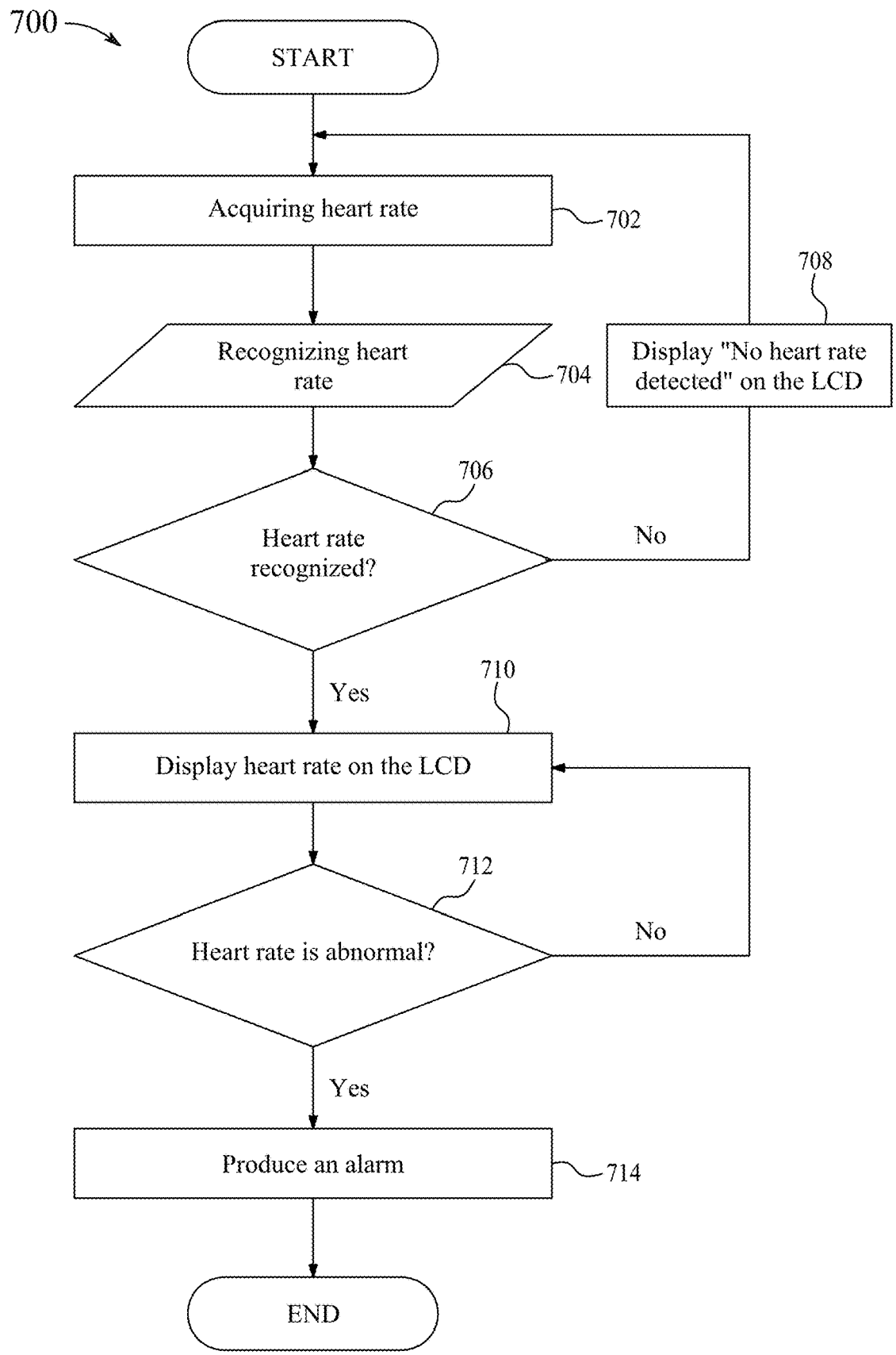
FIG. 7 is an exemplary illustration of a method of determining abnormality of a heart rate of the patient using talking dental glove, according to certain embodiments.

FIG. 7 illustrates a flowchart of a method 700 implemented by the microcontroller 200, according to an aspect of the present disclosure. The method 700 is described in conjunction with FIG. 1A through FIG. 4. At step 702, the microcontroller 200 is configured to acquire the heart rate from the pulse rate sensor 118.

At step 704, the microcontroller 200 is configured to recognize the heart rate based on the pulse rate signals received from the pulse rate sensor 118.

At step 706, when the heart rate is recognized, the microcontroller 200 is configured to, at step 710, display the heart rate on the LCD screen 120. If the heart rate is not recognized, the microcontroller 200 is configured to, at step 708, display a message stating "No heart rate detected" on the LCD screen 120.

At step 712, the microcontroller 200 is configured to determine whether the heart rate is abnormal. As used herein, the term "abnormal" refers to a condition when the heart rate exceeds the heart rate threshold. If the heart rate is determined as abnormal, the microcontroller 200 is configured to, at step 714, produce an alarm. In some aspects, the microcontroller 200 is configured to generate drive signals for the LCD screen 120 and the speaker 122 to provide visual and audio alerts, respectively, regarding the abnormal heart rate.

Figure 8:
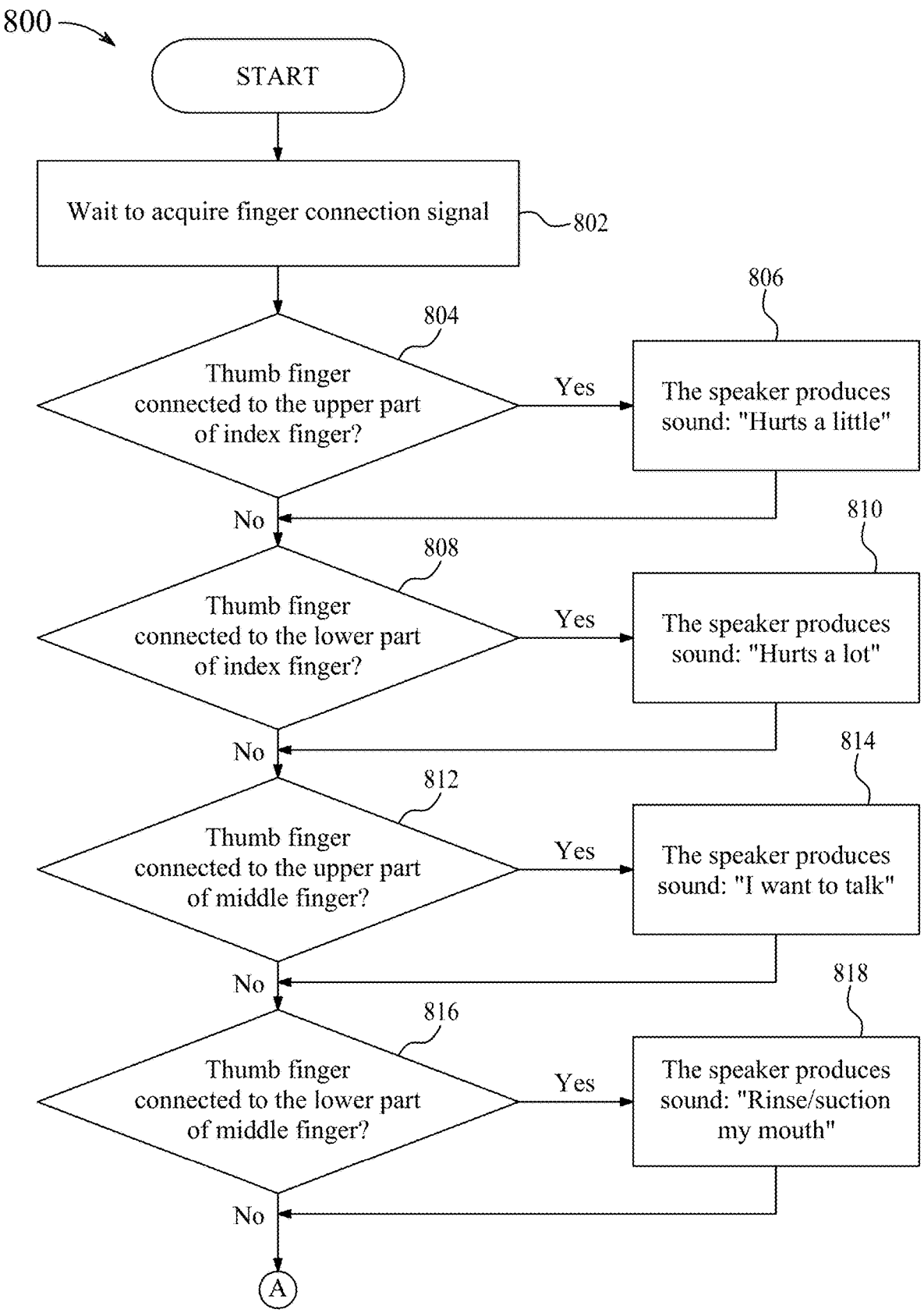
FIG. 8 is an exemplary illustration of a method of outputting audio messages using the talking dental glove to communicate with a dentist, according to certain embodiments.
Figure 8:
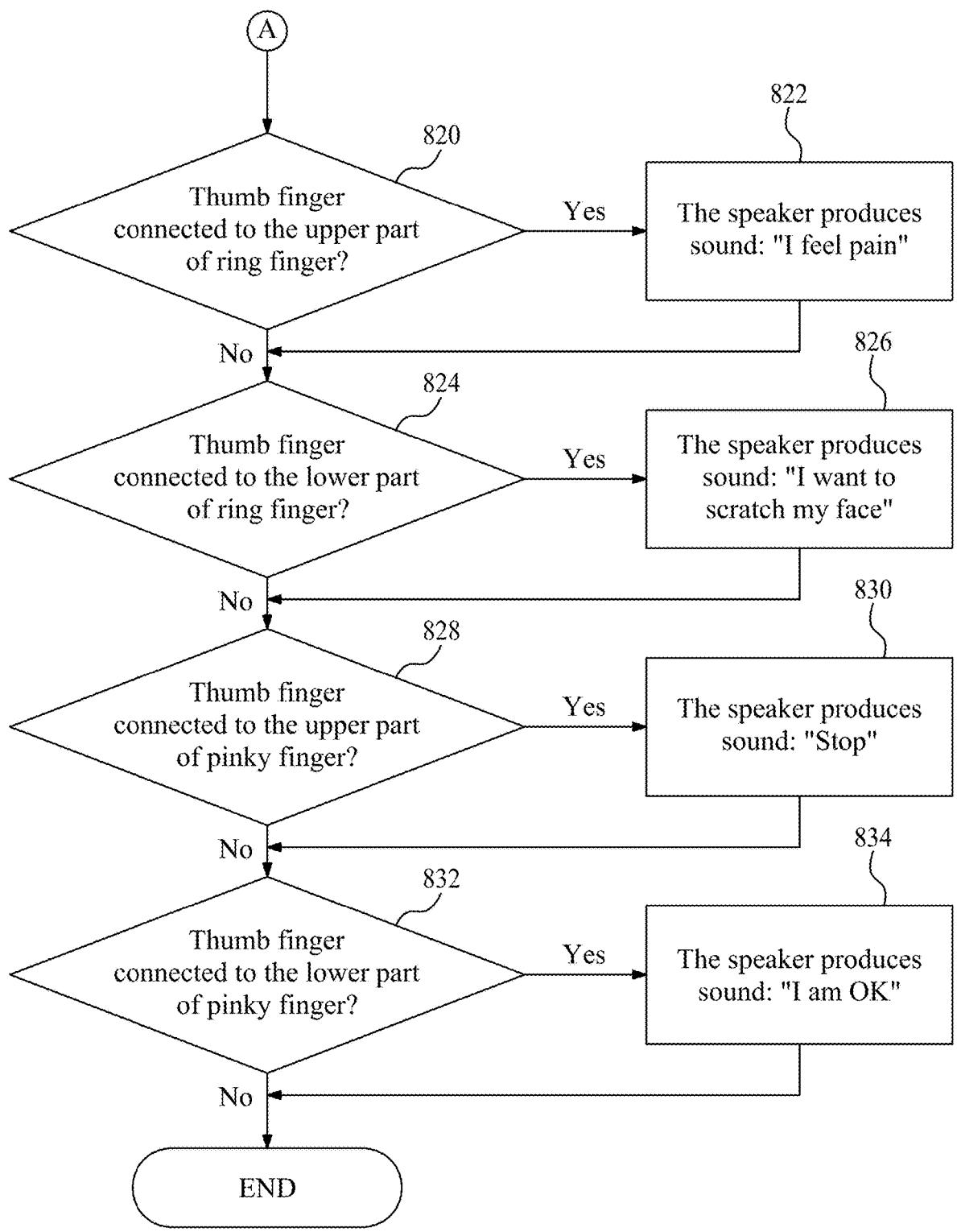

FIG. 8 illustrates a flowchart of a method 800 implemented by the microcontroller 200, according to an aspect of the present disclosure. The method 800 is described in conjunction with FIG. 1A through FIG. 4. At step 802, the microcontroller 200 is configured to wait to acquire a finger connection signal that is generated based on a connection between the trigger contact sensor 124 and one of the plurality of contact sensors. The messages corresponding to the finger connection signals are presented as examples of messages which may represent a contact pattern. The present disclosure is not limited to the exemplary messages of FIG. 8. In some aspects, the messages may be presented in different languages and different formats, such as a male voice or a female voice. Similarly, the age of the patient and other health history may be provided as inputs to the microcontroller 200 via the input unit (not shown), as described before, and a selection of the language and the format of the message may be selected by the the dentist and may be provided as inputs to the microcontroller 200 at the time of configuring the glove 100 before beginning the dental treatment. The format of the message may include choices of a male or female voice, a loudness level and a speech speed. In some aspects, the input unit may be a Bluetooth device communicably connected to the microcontroller 200. In some aspects, the Bluetooth device may be configured to provide the voice output of the messages corresponding to the contact pattern.

At step 804, the microcontroller 200 is configured to determine whether the trigger contact sensor 124 has contacted the upper part of the index finger which includes the index finger contact sensor 126-1. If the microcontroller 200 determines that the contact is established between the trigger contact sensor 124 and the pulse rate sensor 118, the microcontroller 200 is configured to generate drive signals to the speaker 122 to reproduce a message that states "Hurts a little" at step 806.

At step 808, the microcontroller 200 is configured to determine whether the trigger contact sensor 124 has contacted the lower part of the index finger which includes the first center finger contact sensor 128-1, when the trigger contact sensor 124 has not contacted the upper part of the index finger. If the microcontroller 200 determines that the contact is established between the trigger contact sensor 124 and the first center finger contact sensor 128-1, the microcontroller 200 is configured to generate drive signals to the speaker 122 to reproduce a message that states "Hurts a lot" at step 810.

At step 812, the microcontroller 200 is configured to determine whether the trigger contact sensor 124 has contacted the upper part of the middle finger which includes the first fingertip contact sensor 126-2, when the trigger contact sensor 124 has not contacted the lower part of the index finger. If the microcontroller 200 determines that the contact is established between the trigger contact sensor 124 and the first fingertip contact sensor 126-2, the microcontroller 200 is configured to generate drive signals to the speaker 122 to reproduce a message that states "I want to talk" at step 814.

At step 816, the microcontroller 200 is configured to determine whether the trigger contact sensor 124 has contacted the lower part of the middle finger which includes the second center finger contact sensor 128-2, when the trigger contact sensor 124 has not contacted the upper part of the middle finger. If the microcontroller 200 determines that the contact is established between the trigger contact sensor 124 and the second center finger contact sensor 128-2, the microcontroller 200 is configured to generate drive signals to the speaker 122 to reproduce a message that states "Rinse/suction my mouth" at step 818.

At step 820, the microcontroller 200 is configured to determine whether the trigger contact sensor 124 has contacted the upper part of ring finger which include the second fingertip contact sensor 126-3, when the trigger contact sensor 124 has not contacted the lower part of the middle finger. If the microcontroller 200 determines that the contact is established between the trigger contact sensor 124 and the second fingertip contact sensor 126-3, the microcontroller 200 is configured to generate drive signals to the speaker 122 to reproduce a message that states "I feel pain" at step 822.

At step 824, the microcontroller 200 is configured to determine whether the trigger contact sensor 124 has contacted the lower part of the ring finger which includes the third center finger contact sensor 128-3, when the trigger contact sensor 124 has not contacted the upper part of ring finger. If the microcontroller 200 determines that the contact is established between the trigger contact sensor 124 and the third center finger contact sensor 128-3, the microcontroller 200 is configured to generate drive signals to the speaker 122 to reproduce a message that states "I want to scratch my face" at step 826.

At step 828, the microcontroller 200 is configured to determine whether the trigger contact sensor 124 has contacted the upper part of the pinky finger which includes the third fingertip contact sensor 126-4, when the trigger contact sensor 124 has not contacted the lower part of the ring finger. If the microcontroller 200 determines that the contact is established between the trigger contact sensor 124 and the third fingertip contact sensor 126-4, the microcontroller 200 is configured to generate drive signals to the speaker 122 to reproduce a message that states "Stop" at step 830.

At step 832, the microcontroller 200 is configured to determine whether the trigger contact sensor 124 has contacted the lower part of the pinky finger which includes the fourth center finger contact sensor 128-4, when the trigger contact sensor 124 has not contacted the upper part of the pinky finger. If the microcontroller 200 determines that the contact is established between the trigger contact sensor 124 and the fourth center finger contact sensor 128-4, the microcontroller 200 is configured to generate drive signals to the speaker 122 to reproduce a message that states "I am OK" at step 834.

Figure 9:
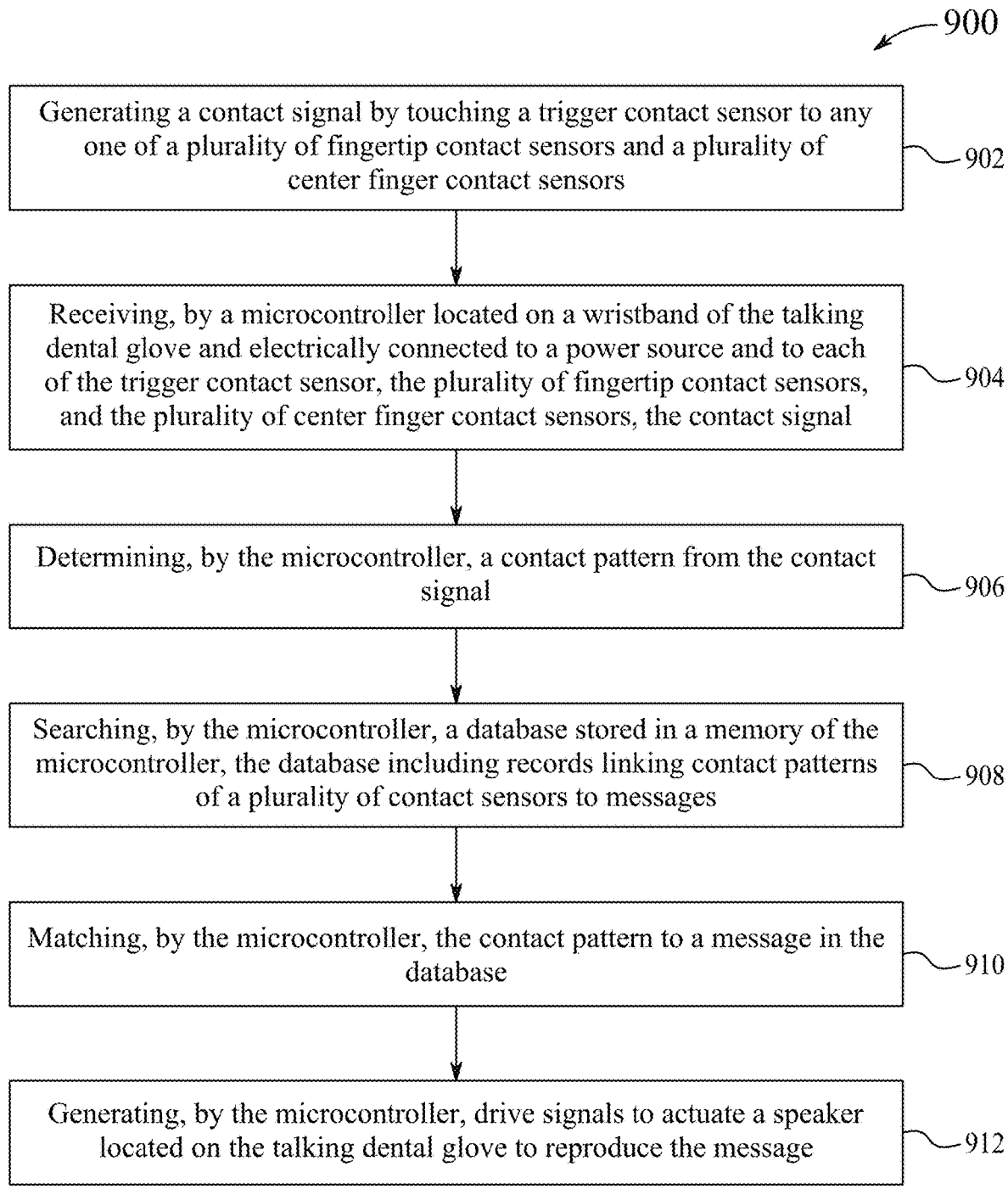
FIG. 9 is a flowchart of a method for using the glove for communication between the dentist and the patient wearing the glove, according to certain embodiments.

FIG. 9 illustrates a flowchart of a method 900 for using the glove 100 for communication between the dentist and the patient wearing the glove 100, according to an aspect of the present disclosure. The method 900 is described in conjunction with FIG. 1A through FIG. 4. At step 902, the method 900 includes generating a contact signal, based on the contact patterns 210, by touching the trigger contact sensor 124 to any one of the plurality of fingertip contact sensors 126 and the plurality of center finger contact sensors 128.

At step 904, the method 900 includes receiving the contact signal, by the microcontroller 200 located on the wristband 114 of the glove 100 and electrically connected to the power source 202 and to each of the trigger contact sensor 124, the plurality of fingertip contact sensors 126, and the plurality of center finger contact sensors 128.

At step 906, the method 900 includes determining, by the microcontroller 200, the contact pattern 210 from the contact signal.

At step 908, the method 900 includes searching, by the microcontroller 200, the database 208 stored in the memory 1004 of the microcontroller 200, the database 208 including records linking contact patterns 210 of the plurality of contact sensors to messages.

At step 910, the method 900 includes matching, by the microcontroller 200, the contact pattern 210 to a message in the database 208.

At step 912, the method 900 includes generating, by the microcontroller 200, drive signals to actuate the speaker 122 located on the glove 100 to reproduce the message.

According to another aspect of the present disclosure, a method for assembling the glove 100 is also provided. The method includes receiving the glove 100 having the glove body 102, the thumb finger sheath 104, the index finger sheath 106, the middle finger sheath 108, the ring finger sheath 110, and the pinky finger sheath 112, and the wristband 114. The method further includes attaching the microcontroller 200 and the power source 202 to the wristband 114; electrically connecting the power source 202 to the microcontroller 200; attaching the LCD screen 120 to the wristband 114; electrically connecting the LCD screen 120 to the power source 202; connecting the LCD screen 120 to the microcontroller 200; attaching the speaker 122 to the wristband 114; electrically connecting the speaker 122 to the power source 202; connecting the speaker 122 to the microcontroller 200; attaching the trigger contact sensor 124 to the thumb pad position of the thumb finger sheath 104; electrically connecting the trigger contact sensor 124 to the microcontroller 200; attaching each of the plurality of fingertip contact sensors 126 to the fingertip position of the index finger sheath 106, the middle finger sheath 108, the ring finger sheath 110, and the pinky finger sheath 112; electrically connecting each of the plurality of fingertip contact sensors 126 to the microcontroller 200; attaching each of the plurality of center finger contact sensors 128 to a region between the glove body 102 and the fingertip position of the index finger sheath 106, the middle finger sheath 108, the ring finger sheath 110, and the pinky finger sheath 112; electrically connecting each of the plurality of fingertip contact sensors 126 to the microcontroller 200; attaching the suction button 116 to the side position of the glove body 102 beneath a base of the index finger sheath 106; electrically connecting the suction button 116 to the microcontroller 200; and attaching the microcontroller 200 to the valve 204 of the mouth fluid suction tool 206, where the valve 204 is configured to control a vacuum of the mouth fluid suction tool 206, and where the microcontroller 200 is configured to actuate the valve 204 to control the vacuum when the trigger contact sensor 124 touches the suction button 116.

To this end, it will be understood that glove 100 of the present disclosure simplifies the process of communication between the patient and the dentist, besides enhancing level of both safety and patient satisfaction by: (a) producing sounds that correspond to text messages based on the contact pattern to allow the patient to communicate with the dentist; (b) minimizing risk related to health by monitoring and displaying the heart rate in real time during the dental treatment; (c) producing an alarm when abnormal heart rate is detected; (d) allowing the patient to actuate the suction device when desired. Since the communication may be established by the glove 100, patients of all age may use it without requirement of intense training. Also, the glove 100 of the present disclosure aids communication between the patient and the dentist without the need of any external device, such as a smartphone.

Figure 10:
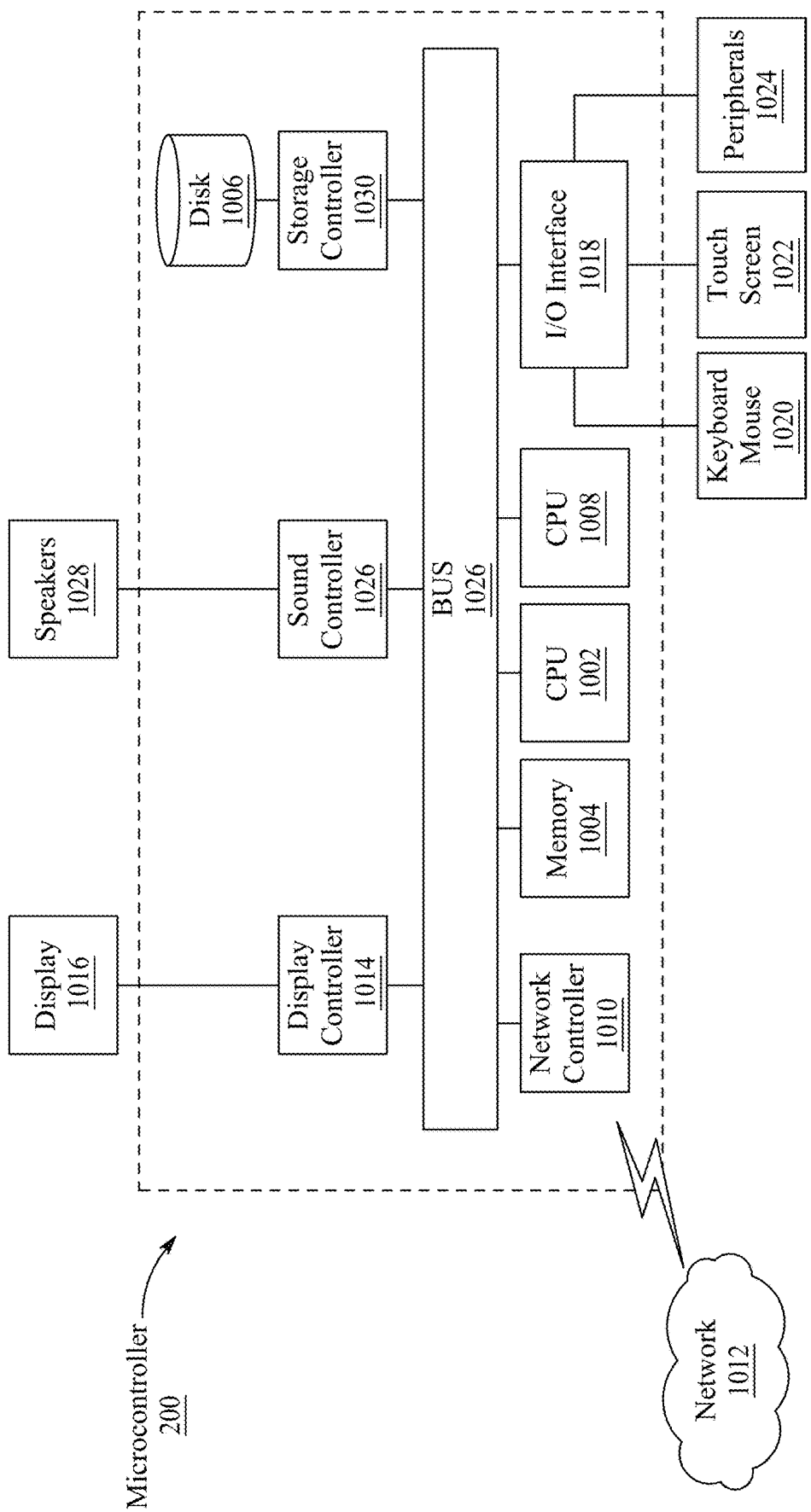
FIG. 10 is an illustration of distributed components which may share processing with the computing hardware, according to certain embodiments.

Next, further details of the hardware description of the computing environment according to exemplary embodiments is described with reference to FIG. 10. In FIG. 10, the microcontroller 200 is embodied as a computing device which includes a CPU 1002 which performs the processes described above/below. The process data and instructions may be stored in memory 1004. These processes and instructions may also be stored on a storage medium disk 1006 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with the CPU 1002, 1008 and an operating system such as Microsoft Windows 7, Microsoft Windows 10, Microsoft Windows 11, UNIX, Solaris, LINUX, Apple MAC-OS, and other systems known to those skilled in the art.

The hardware elements in order to achieve the computing device may be realized by various circuitry elements, known to those skilled in the art. For example, the CPU 1002 or 1008 may be a Xenon or Core processor from Intel of America or an Opteron processor from AMD of America, or may be other processor types that would be recognized by one of ordinary skill in the art. Alternatively, the CPU 1002, 1008 may be implemented on an FPGA, ASIC, PLD or using discrete logic circuits, as one of ordinary skill in the art would recognize. Further, the CPU 1002, 1008 may be implemented as multiple processors cooperatively working in parallel to perform the instructions of the inventive processes described above.

The computing device in FIG. 10 also includes a network controller 1010, such as an Intel Ethernet PRO network interface card from Intel Corporation of America, for interfacing with a network 1012. As can be appreciated, the network 1012 can be a public network, such as the Internet, or a private network such as an LAN or WAN network, or any combination thereof and can also include PSTN or ISDN sub-networks. The network 1012 can also be wired, such as an Ethernet network, or can be wireless such as a cellular network including EDGE, 3G, 4G and wireless cellular systems. The wireless network can also be WiFi, Bluetooth, or any other wireless form of communication that is known.

The computing device further includes a display controller 1014, such as a NVIDIA GeForce GTX or Quadro graphics adaptor from NVIDIA Corporation of America for interfacing with a display 1016, such as a Hewlett Packard HPL2445w LCD monitor. A general purpose I/O interface 1018 interfaces with a keyboard and/or mouse 1020 as well as a touch screen panel 1022 on or separate from the display 1016. The general purpose I/O interface 1018 also connects to a variety of peripherals 1024 including printers and scanners, such as an OfficeJet or DeskJet from Hewlett Packard.

A sound controller 1026 is also provided in the computing device such as Sound Blaster X-Fi Titanium from Creative, to interface with speakers/microphone 1028 thereby providing sounds and/or music.

A general purpose storage controller 1030 connects the storage medium disk 1006 with a communication bus 1032, which may be an ISA, EISA, VESA, PCI, or similar, for interconnecting all of the components of the computing device. A description of the general features and functionality of the display 1016, the keyboard and/or mouse 1020, as well as the display controller 1014, the storage controller 1030, the network controller 1010, the sound controller 1026, and the general purpose I/O interface 1018 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset. The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A talking dental glove, comprising:
each disposed on an outer surface of the glove:
a plurality of contact sensors, wherein each contact sensor is located on a different finger position of the talking dental glove;
a suction button;
a pulse rate sensor configured to generate pulse rate signals;
an LCD screen;
a speaker;
a power source; and
a microcontroller connected to the power source, the plurality of contact sensors, the pulse rate sensor, the LCD screen, and the speaker.

2. The talking dental glove of claim 1, wherein the microcontroller is configured to:
receive the pulse rate signals,
determine a heart rate from the pulse rate signals,
render the heart rate and the pulse rate signals on the LCD screen,
determine whether the heart rate exceeds a heart rate threshold; and
when the heart rate exceeds the heart rate threshold:
actuate the speaker to generate an audible alert; and
render a visual alert on the LCD screen.

3. The talking dental glove of claim 1, further comprising:
a database stored in a memory of the microcontroller, wherein the database includes records linking contact patterns of the plurality of contact sensors to messages;
wherein the microcontroller is configured to receive each contact pattern, perform a search of the database, and match the contact pattern to a message in the database; and
wherein the microcontroller is further configured to generate drive signals to actuate the speaker to reproduce the message.

4. The talking dental glove of claim 3, further comprising:
a glove body;
a thumb finger sheath, an index finger sheath, a middle finger sheath, a ring finger sheath, and a pinky finger sheath each connected to the glove body; and
a wristband connected to the glove body, wherein the microcontroller, the LCD screen and the speaker are located on the wristband.

5. The talking dental glove of claim 4, wherein the pulse rate sensor is located on the index finger sheath at a fingertip position.

6. The talking dental glove of claim 4, wherein the suction button is located on a side of the glove body beneath a base of the index finger sheath.

7. The talking dental glove of claim 6, wherein the suction button is connected to a valve of a mouth fluid suction tool, wherein touching the suction button opens the valve.

8. The talking dental glove of claim 4, wherein the plurality of contact sensors comprise:
a trigger contact sensor located on a thumb pad position of the thumb finger sheath;
a plurality of fingertip contact sensors, wherein a fingertip contact sensor is connected to a fingertip position of each of the index finger sheath, the middle finger sheath, the ring finger sheath, and the pinky finger sheath; and
a plurality of center finger contact sensors, wherein each center finger contact sensor is connected to a region between the glove body and the fingertip position of each of the index finger sheath, the middle finger sheath, the ring finger sheath, and the pinky finger sheath.

9. The talking dental glove of claim 8, wherein the contact pattern includes signals generated by touching the trigger contact sensor to one of the fingertip contact sensors on the index finger sheath, the middle finger sheath, the ring finger sheath, and the pinky finger sheath.

10. The talking dental glove of claim 8, wherein the contact pattern further includes signals generated by touching the trigger contact sensor to one of the center finger contact sensors on the index finger sheath, the middle finger sheath, the ring finger sheath, and the pinky finger sheath.

11. The talking dental glove of claim 10, wherein the microcontroller is configured generate the drive signals to actuate the speaker to reproduce:

a first message when the trigger contact sensor touches an index finger fingertip contact sensor;
a second message when the trigger contact sensor touches a middle finger fingertip contact sensor;
a third message when the trigger contact sensor touches a ring finger fingertip contact sensor;
a fourth message when the trigger contact sensor touches a pinky finger fingertip contact sensor;
a fifth message when the trigger contact sensor touches an index finger center finger contact sensor;
a sixth message when the trigger contact sensor touches a middle finger center finger contact sensor;
a seventh message when the trigger contact sensor touches a ring finger center finger contact sensor; and
an eighth message when the trigger contact sensor touches a pinky finger center finger contact sensor.

12. The talking dental glove of claim 8, wherein the suction button is connected to the microcontroller.

13. The talking dental glove of claim 12, further comprising:
a mouth fluid suction tool;
a valve connected to the mouth fluid suction tool, wherein the valve is configured to control a vacuum of the mouth fluid suction tool; and
wherein the microcontroller is connected to the valve and is configured to actuate the valve to control the vacuum when the trigger contact sensor touches the suction button.

14. A method for using a talking dental glove for communication between a patient wearing the talking dental glove and a dentist, comprising:
generating a contact signal by touching a trigger contact sensor to any one of a plurality of fingertip contact sensors and a plurality of center finger contact sensors;
receiving, by a microcontroller located on a wristband of the talking dental glove and electrically connected to a power source and to each of the trigger contact sensor, the plurality of fingertip contact sensors, and the plurality of center finger contact sensors, the contact signal;
determining, by the microcontroller, a contact pattern from the contact signal;
searching, by the microcontroller, a database stored in a memory of the microcontroller, the database including records linking contact patterns of a plurality of contact sensors to messages;
matching, by the microcontroller, the contact pattern to a message in the database;
generating, by the microcontroller, drive signals to actuate a speaker located on the talking dental glove to reproduce the message;
generating a suction signal by touching the trigger contact sensor to a suction button located on the talking dental glove; and
receiving, by the microprocessor, the suction signal; and
actuating, by the microprocessor, a valve of a mouth fluid suction tool, wherein actuating the valve controls a vacuum in the mouth fluid suction tool, based on the suction signal.

15. The method of claim 14, further comprising:
receiving, by the microcontroller, pulse rate signals from a pulse rate sensor located on the talking dental glove and electrically connected to the microcontroller;
determining, by the microcontroller, a heart rate from the pulse rate signals;
rendering, by the microcontroller, the heart rate and the pulse rate signals on an LCD screen electrically connected to the microcontroller;
determining, by the microcontroller, whether the heart rate exceeds a heart rate threshold;
actuating, by the microcontroller, the speaker to generate an audible alert when the heart rate exceeds the heart rate threshold; and
rendering, by the microcontroller, a visual alert on the LCD screen when the heart rate exceeds the heart rate threshold.

16. The method claim 14, further comprising:
generating, by the microcontroller, the drive signals configured to actuate the speaker to reproduce:
a first message when the trigger contact sensor touches an index finger fingertip contact sensor;
a second message when the trigger when the trigger contact sensor touches a middle finger fingertip contact sensor;
a third message when the trigger when the trigger contact sensor touches a ring finger fingertip contact sensor;
a fourth message when the trigger when the trigger contact sensor touches a pinky finger fingertip contact sensor;
a fifth message when the trigger contact sensor touches an index finger center finger contact sensor;
a sixth message when the trigger contact sensor touches a middle finger center finger contact sensor;
a seventh message when the trigger contact sensor touches a ring finger center finger contact sensor; and
an eighth message when the trigger contact sensor touches a pinky finger center finger contact sensor.

17. A method for assembling a talking dental glove, comprising:
receiving the talking dental glove having a glove body, a thumb finger sheath, an index finger sheath, a middle finger sheath, a ring finger sheath, and a pinky finger sheath, and a wristband;
attaching a microcontroller to the wristband;
attaching a power source to the wristband;
electrically connecting the power source to the microcontroller;
attaching an LCD screen to the wristband;
electrically connecting the LCD screen to the power source;
connecting the LCD screen to the microcontroller;
attaching a speaker to the wristband;
electrically connecting the speaker to the power source;
connecting the speaker to the microcontroller;
attaching a trigger contact sensor to a thumb pad position of the thumb finger sheath;
electrically connecting the trigger contact sensor to the microcontroller;
attaching each of a plurality of fingertip contact sensors to a fingertip position of a different one of the index finger sheath, the middle finger sheath, the ring finger sheath, and the pinky finger sheath;
electrically connecting each of the plurality of fingertip contact sensors to the microcontroller;
attaching each of a plurality of center finger contact sensors to a region between the glove body and the fingertip position of the index finger sheath, the middle finger sheath, the ring finger sheath, and the pinky finger sheath;
electrically connecting each of the plurality of fingertip contact sensors to the microcontroller;

attaching a suction button to a side position of the glove body beneath a base of the index finger sheath;

electrically connecting the suction button to the microcontroller; and attaching the microcontroller to a valve of a mouth fluid suction tool, wherein the valve is configured to control a vacuum of the mouth fluid suction tool, and wherein the microcontroller is configured to actuate the valve to control the vacuum when the trigger contact sensor touches the suction button.

18. The method of claim 17, further comprising:

attaching a pulse rate sensor to a fingertip position of the index finger sheath;

electrically connecting the pulse rate sensor to the microcontroller, wherein the pulse rate sensor is configured to generate pulse rate signals;

configuring the microcontroller to perform the steps of:
 receiving the pulse rate signals;
 determining a heart rate from the pulse rate signals;
 rendering the heart rate and the pulse rate signals on the LCD screen;
 determining whether the heart rate exceeds a heart rate threshold;
 when the heart rate exceeds the heart rate threshold, actuating the speaker to generate an audible alert; and
 rendering a visual alert on the LCD screen.

19. The method of claim 17, further comprising:

configuring the microcontroller to generate drive signals to actuate the speaker to reproduce:

a first message when the trigger contact sensor touches an index finger fingertip contact sensor;

a second message when the trigger when the trigger contact sensor touches a middle finger fingertip contact sensor;

a third message when the trigger when the trigger contact sensor touches a ring finger fingertip contact sensor;

a fourth message when the trigger when the trigger contact sensor touches a pinky finger fingertip contact sensor;

a fifth message when the trigger contact sensor touches an index finger center finger contact sensor;

a sixth message when the trigger contact sensor touches a middle finger center finger contact sensor;

a seventh message when the trigger contact sensor touches a ring finger center finger contact sensor; and an eighth message when the trigger contact sensor touches a pinky finger center finger contact sensor.

* * * * *